(12) United States Patent
Vankipuram et al.

(10) Patent No.: US 11,474,603 B2
(45) Date of Patent: Oct. 18, 2022

(54) EXTENDED REALITY GRASP CONTROLLER

(71) Applicant: Hewlett-Packard Development Company, L.P., Spring, TX (US)

(72) Inventors: Mithra Vankipuram, Palo Alto, CA (US); Hiroshi Horii, Palo Alto, CA (US); Rafael Ballagas, Palo Alto, CA (US)

(73) Assignee: Hewlett-Packard Development Company, L.P., Spring, TX (US)

( * ) Notice: Subject to any disclaimer, the term of this patent is extended or adjusted under 35 U.S.C. 154(b) by 0 days.

(21) Appl. No.: 17/414,346

(22) PCT Filed: Jun. 12, 2019

(86) PCT No.: PCT/US2019/036792
§ 371 (c)(1),
(2) Date: Jun. 16, 2021

(87) PCT Pub. No.: WO2020/251566
PCT Pub. Date: Dec. 17, 2020

(65) Prior Publication Data
US 2022/0100273 A1 Mar. 31, 2022

(51) Int. Cl.
*G06F 3/01* (2006.01)
*A61B 5/313* (2021.01)
*A61B 5/00* (2006.01)
*A61N 1/04* (2006.01)

(52) U.S. Cl.
CPC .............. *G06F 3/014* (2013.01); *A61B 5/313* (2021.01); *A61B 5/6825* (2013.01); *A61N 1/0456* (2013.01); *A61N 1/0472* (2013.01); *G06F 3/015* (2013.01); *G06F 3/016* (2013.01); *G06F 2203/011* (2013.01)

(58) Field of Classification Search
None
See application file for complete search history.

(56) References Cited

U.S. PATENT DOCUMENTS

| 5,764,164 | A | 6/1998 | Cartabiano et al. |
| 9,342,151 | B2 | 5/2016 | Gu |
| 9,360,944 | B2 | 6/2016 | Pinault |
| 2005/0172734 | A1* | 8/2005 | Alsio ................... G06F 3/0346 73/865.4 |
| 2014/0018166 | A1 | 1/2014 | Guild et al. |

(Continued)

FOREIGN PATENT DOCUMENTS

EP 1523725 B1 9/2010

OTHER PUBLICATIONS

Lang, Ben, "First Look at Valve's New VR Controller Prototype." Oct. 12, 2016. Available at: https://www.roadtovr.com/first-look-at-valves-new-vr-controller-prototype/.

*Primary Examiner* — Carl Adams
(74) *Attorney, Agent, or Firm* — Tong Rea Bentley & Kim LLC

(57) ABSTRACT

In example implementations, an apparatus is provided. The apparatus includes a body portion and a plurality of legs movably coupled to the body portion. The body portion is to rest on a backside of a hand of a user. Each one of the plurality of legs include a curved portion to fit between fingers of a user. Respective ends of the plurality of legs are to contact a palm of the user.

11 Claims, 7 Drawing Sheets

(56) References Cited

U.S. PATENT DOCUMENTS

| | | |
|---|---|---|
| 2016/0239087 A1 | 8/2016 | Shih et al. |
| 2016/0274662 A1 | 9/2016 | Rimon et al. |
| 2017/0083091 A1 | 3/2017 | Okamoto |
| 2017/0235364 A1* | 8/2017 | Nakamura ............... G06F 3/016 345/156 |
| 2018/0335843 A1 | 11/2018 | Erivantcev et al. |

* cited by examiner

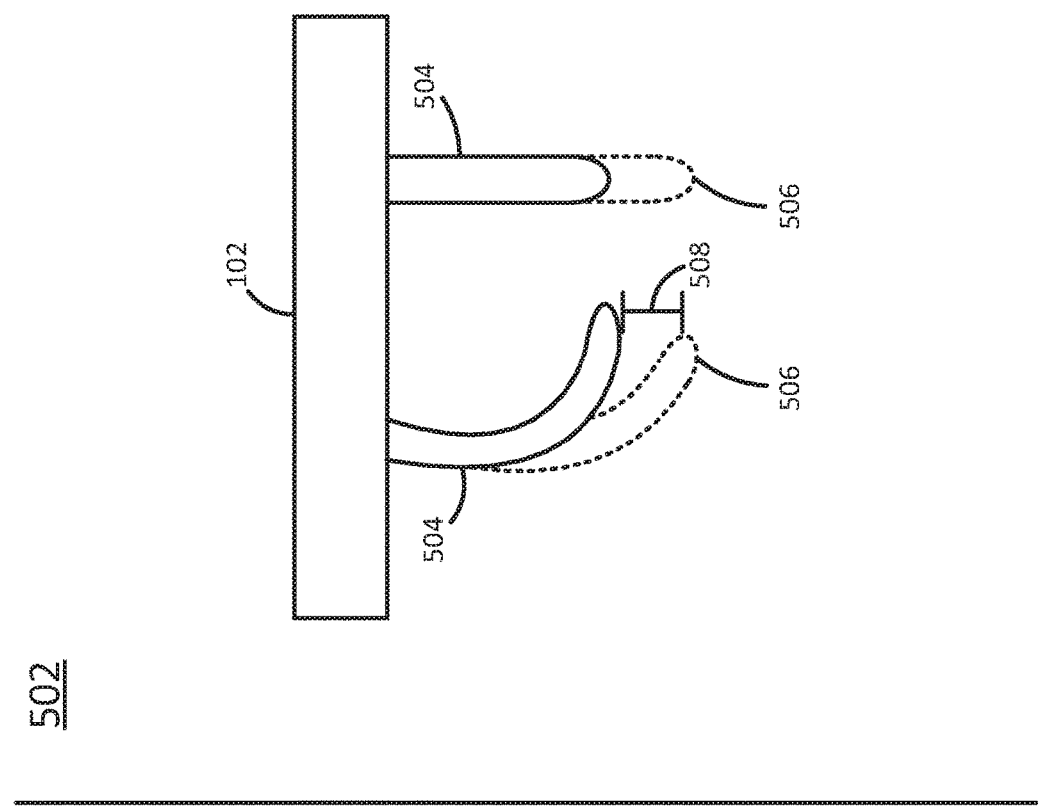
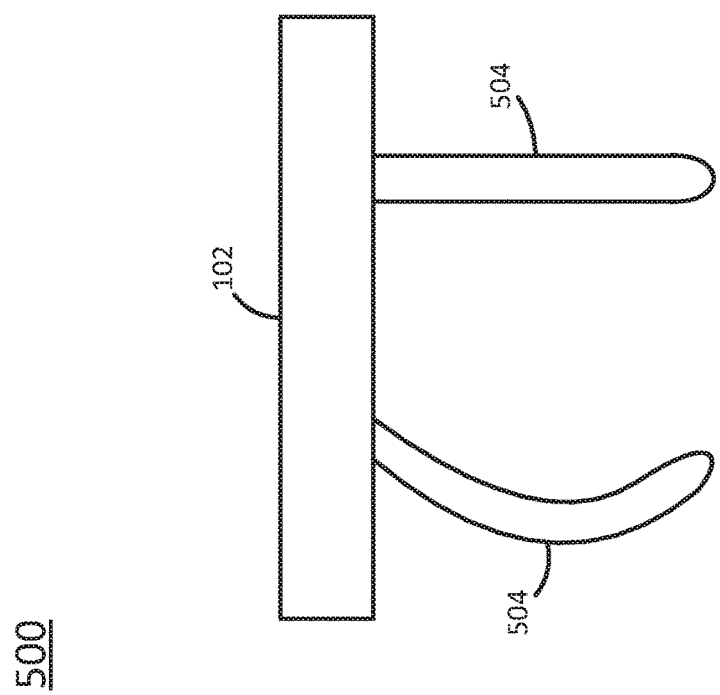
FIG. 5

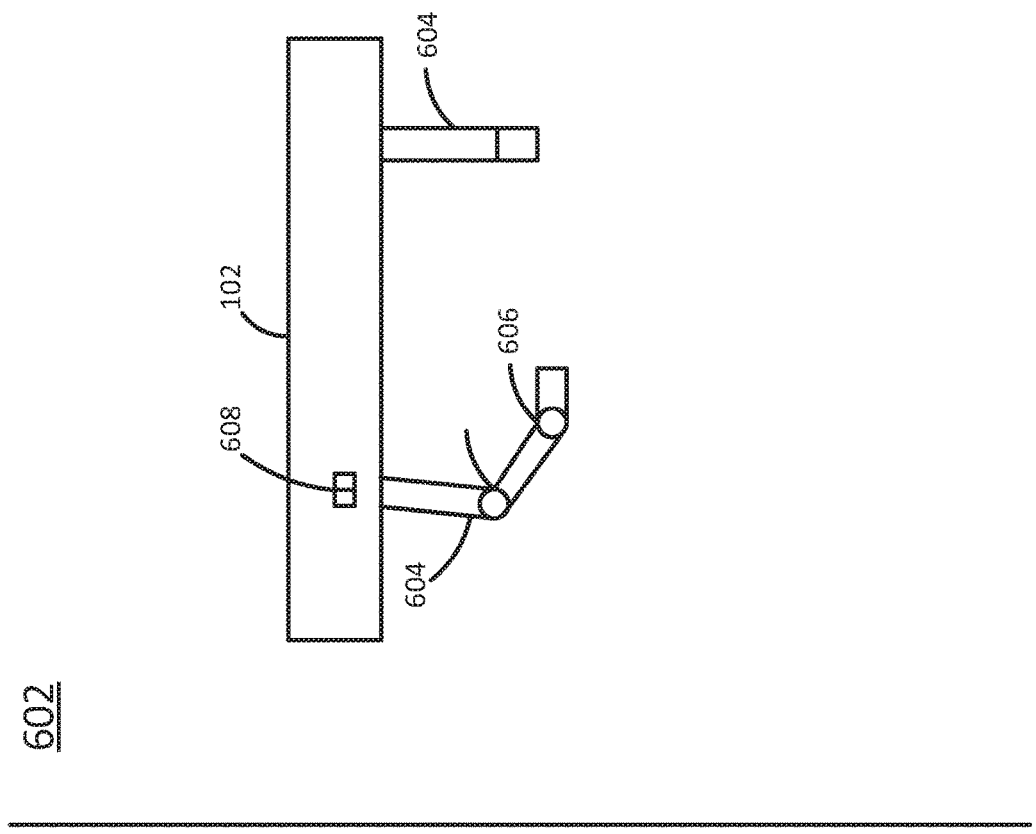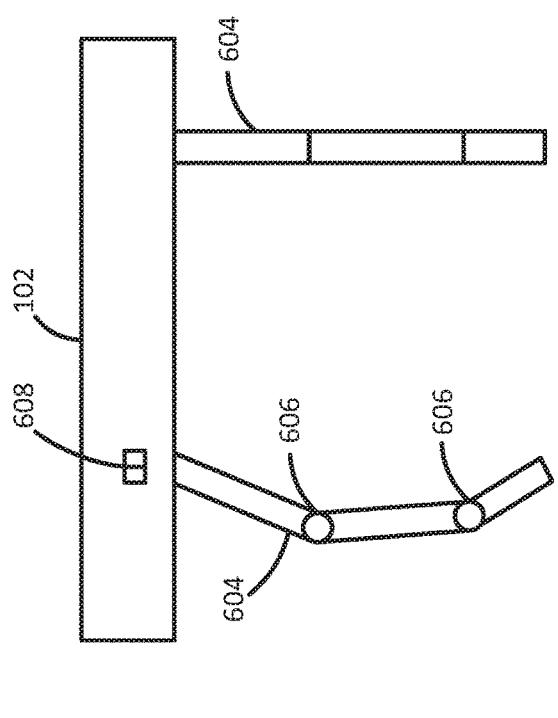
FIG. 6

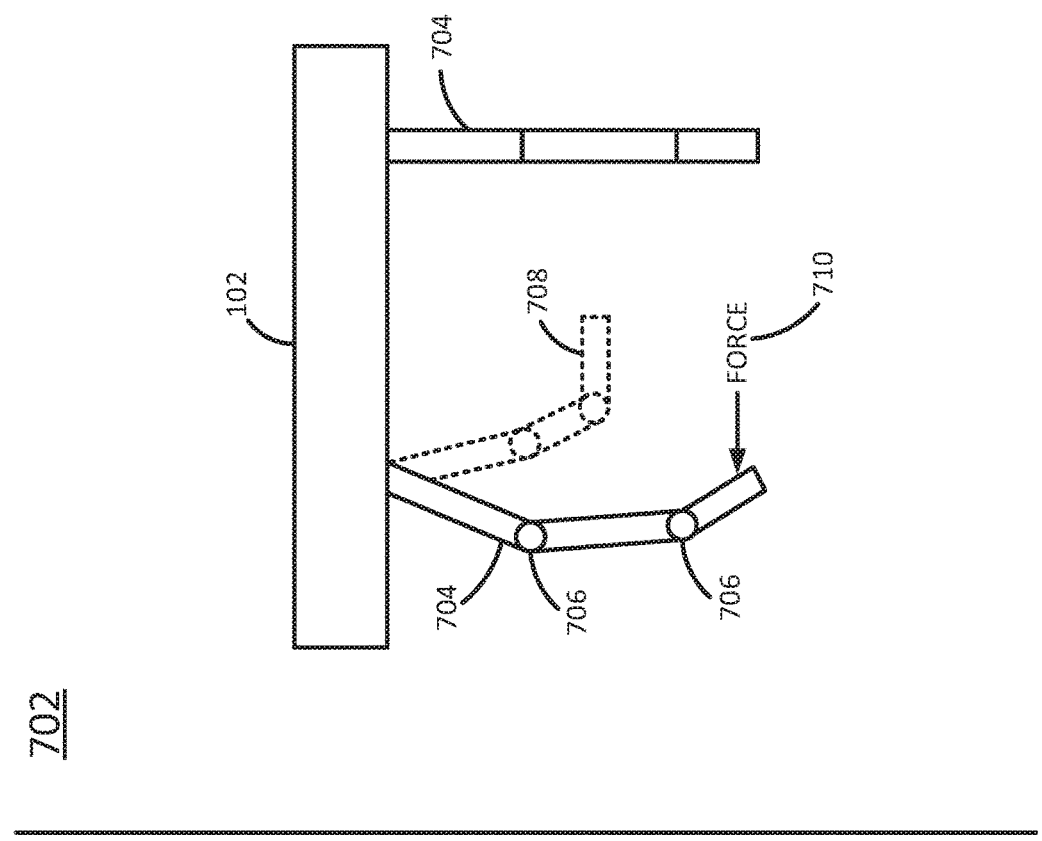

EXTENDED REALITY GRASP CONTROLLER

BACKGROUND

Virtual reality (VR) applications provide new experiences for users. The VR applications can provide an artificial environment created via software. The VR systems may include a range of hardware. For example, a VR systems may include an entire enclosure where the user can feel movement as the enclosure moves, or may include a head mounted display that can be worn by the user.

BRIEF DESCRIPTION OF THE DRAWINGS

FIG. 5 illustrates example positions of the legs of the XR grasp controller fabricated from a shape morphing material;

FIG. 6 illustrates example positions of the legs of the XR grasp controller operated via a switch; and FIG. 7 illustrates example positions of the legs of the XR grasp controller deployed with spring loaded hinge.

DETAILED DESCRIPTION

Examples described herein provide an XR grasp controller. In one example, extended reality (XR) may be defined to include virtual reality (VR) devices and applications, augmented reality (AR) devices and applications, mixed reality (MR) devices and applications, and the like.

As discussed above, VR applications provide new experiences for users. Some VR systems include a head mounted display that can be used with gloves that provide controls.

However, gloves may be cumbersome to wear and can be uncomfortable as the hand becomes hot and sweaty inside of the glove. In addition, with the glove, a user may not be able to provide commands when grasping a virtual object with the glove.

Examples herein provide a grasp controller that can be placed on the back of a hand of the user. The design of the grasp controller allows the fingers of the user to remain free for use. The grasp controller may detect movement of the hand to provide various control inputs to the XR environment, while the user may use his or her fingers to grasp or interact with various objects in the XR environment.

In some examples, the XR grasp controller may also include biometric sensors that can be used to collect biometric data. The biometric data can be collected to make adjustments to the XR environment, adjust the haptic feedback provided by the XR grasp controller, and the like.

The design of the XR grasp controller allows the XR grasp controller to be easily worn by a user. Users with low finger dexterity can still wear the XR grasp controller as the XR grasp controller is designed with legs that may slide between the fingers of the user.

In addition, the design of the XR grasp controller may provide optimal positioning for the biometric sensors. For example, some biometric sensors may work better when in contact with the palm of a user, as opposed to the back of a user's hand or the fingertips of the user. Thus, the present disclosure provides an efficient design that allows the XR grasp controller to be easily worn and optimally positions the biometric sensors to collect biometric data.

Figure 1:
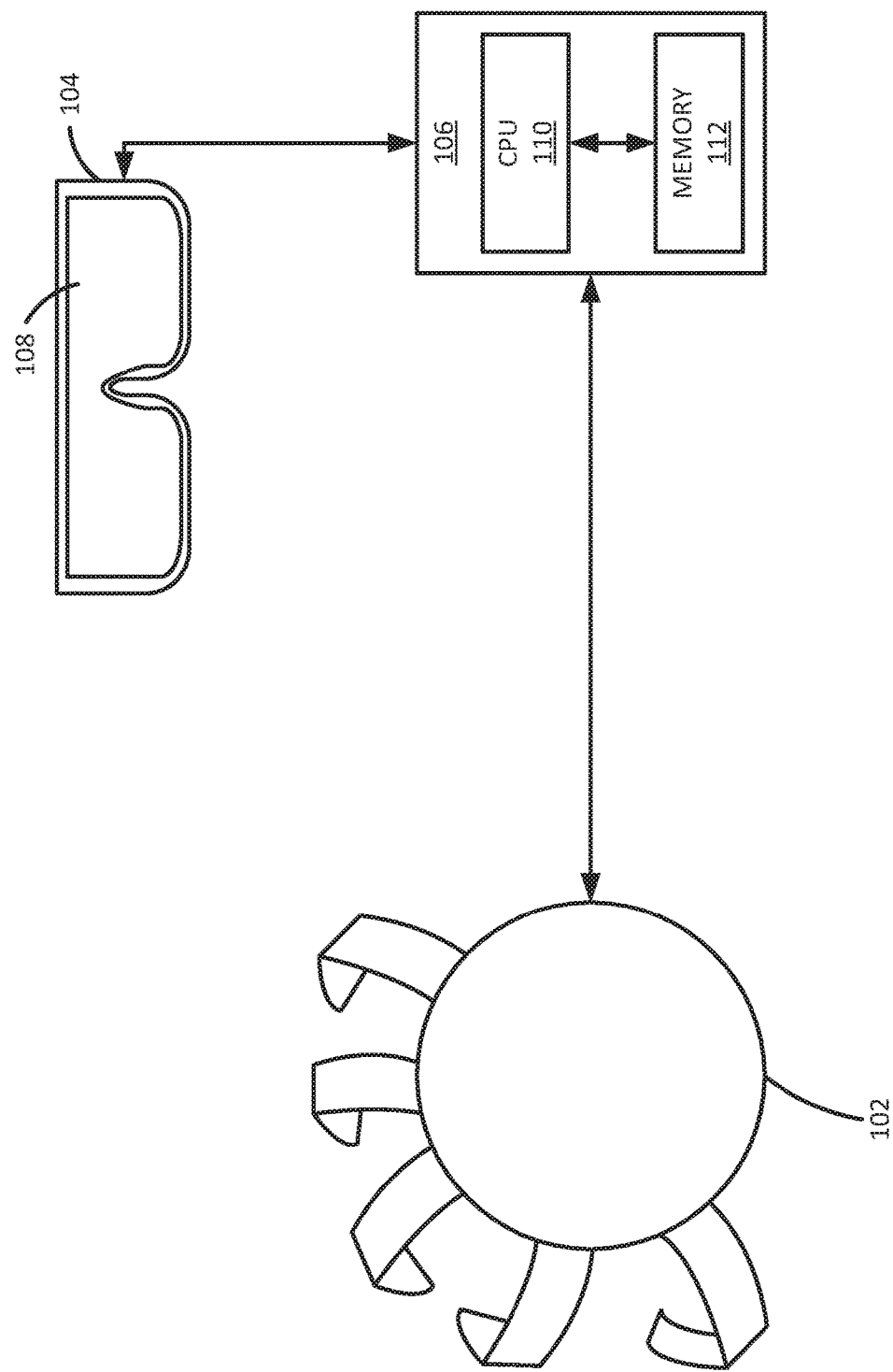
FIG. 1 is a block diagram of a extended reality (XR) system with an XR grasp controller of the present disclosure.

FIG. 1 illustrates an example XR system 100 of the present disclosure. As discussed above, XR may include VR, AR, or MR. In one example, the XR system 100 may include an XR grasp controller 102, a head mounted display (HMD) 104, and a computing device 106. The XR grasp controller 102 and the HMD 104 may be communicatively coupled, via a wired or wireless connection, to the computing device 106.

In one example, the computing device 106 may include a processor (CPU) 110 and a memory 112. The memory 112 may be a non-transitory computer readable medium, such as a random access memory (RAM), a read only memory (ROM), a hard disk drive, a solid state drive, and the like. The processor 110 may be communicatively coupled to the memory 112 to execute instructions stored in the memory 112. For example, the memory 112 may store instructions for an XR application. The XR application may display a XR environment that can be shown on the HMD 104 and receive control inputs and other types of information from the XR grasp controller 102.

In one example, the HMD 104 may include a display 108. The display 108 may show the XR environment associated with the XR application. It should be noted that the HMD 104 has been simplified for ease of explanation. The HMD 104 may include other components that are not shown (e.g., a speaker, a microphone, and the like). In one example, the computing device 106 may be deployed in the HMD 104. In other words, the components of the computing device 106 and the HMD 104 may be combined and the XR grasp controller 102 may be communicatively coupled to the HMD 104.

In one example, the XR grasp controller 102 may be designed to grasp onto a hand of a user. Thus, the XR grasp controller 102 may be more efficient to put on than a glove. For example, the legs of the XR grasp controller 102 can be positioned between the fingers of the user, as discussed in further details below. The positioning of the legs of the XR grasp controller 102 may also allow the fingers of a user to remain free for other use rather than holding onto a controller. In addition, since the hand of the user is not inside of a glove, the XR grasp controller 102 may be more comfortable to wear.

Lastly, the design of the XR grasp controller 102 may allow a single XR grasp controller 102 to be worn by any sized hand. In other words, the XR grasp controller 102 may be a "one size fits all" design, rather than a glove that may have different sizes for different sized hands. Having a single sized XR grasp controller 102 may reduce inventory and costs.

Figure 2:
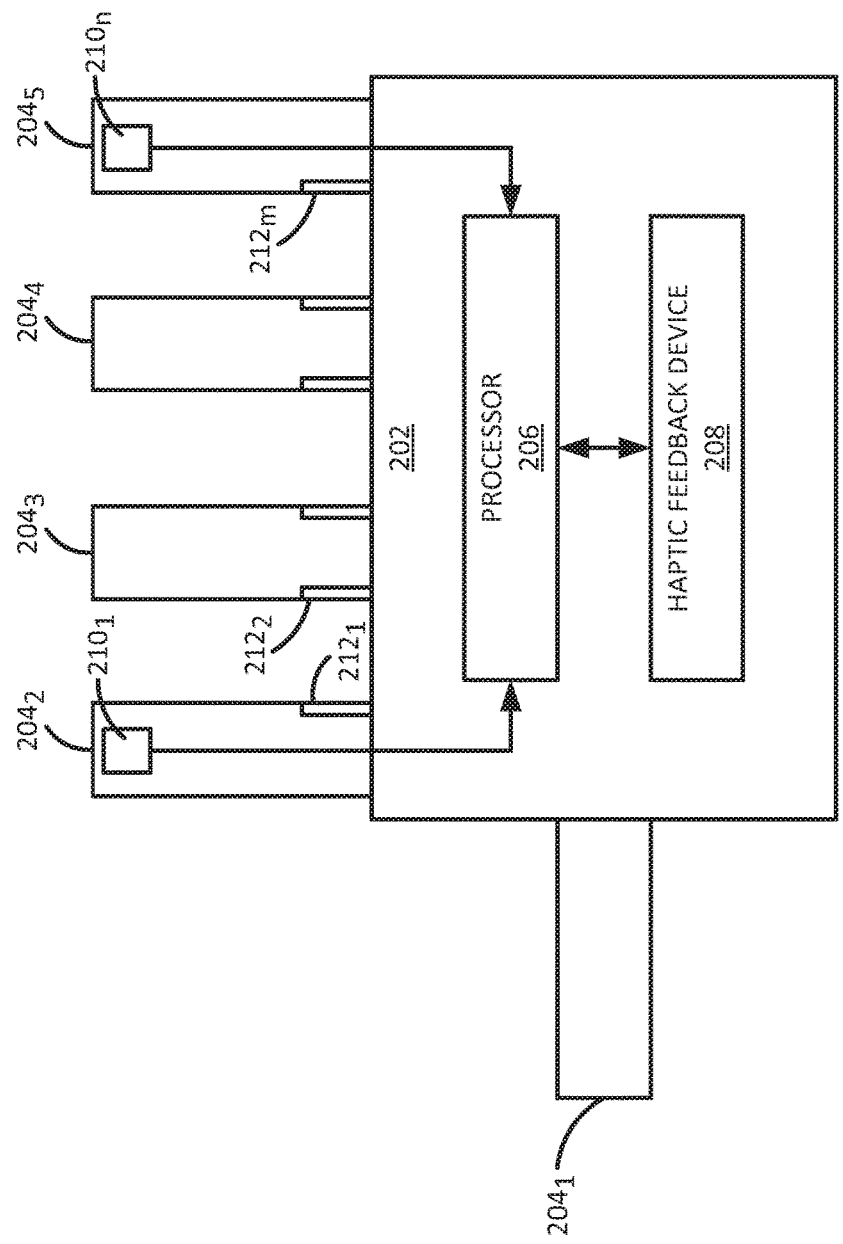
FIG. 2 is a block diagram of an example extended reality (XR) grasp controller of the present disclosure.

FIG. 2 illustrates a functional block diagram of the XR grasp controller 102. In one example, the XR grasp controller 102 may include a body portion 202 and a plurality of legs $204_1$-$204_5$ (hereinafter also referred to individually as a leg 204 or collectively as legs 204).

The body portion 202 may include a processor 206 and a haptic feedback device 208. The processor 206 may be communicatively coupled to the haptic feedback device 208. The haptic feedback device 208 may provide haptic feedback in response to events that occur in the XR environment.

In one example, the haptic feedback device 208 may be located on a bottom side of the body portion 202 to contact a back of the hand of the user. The haptic feedback device 208 may be deployed as a transcutaneous electrical nerve stimulation (TENS) electrode that contacts the back of the hand of the user. The electrode may provide different types of pulses or stimulation to generate the haptic feedback. In one example, the haptic feedback device 208 may be any type of device that can provide haptic feedback such as stretching the skin of a user, providing texture, providing a pulse or vibration, and the like.

The legs 204 may be movably coupled to the body portion 202 and may be positioned to fit between fingers of a user. At least one of the legs 204 may include a biometric sensor $210_1$ to $210_n$ (hereinafter also referred to individually as a biometric sensor 210 or collectively as biometric sensors 210) to collect biometric data of a user. The biometric sensor 210 may be located at a tip or end of a respective leg 204.

The design of the legs 204 may be such that the tip or end of the legs 204 contacts a palm of a user. As a result, the design of the legs 204 may allow the biometric sensor 210 to be properly positioned against the palm of a user to collect biometric data of the user.

For example, some biometric sensors 210 may collect biometric data more accurately when in contact with a palm of the user rather than other portions of the hand of the user. Thus, the legs 204 may properly position the biometric sensor 210 when the legs 204 are in a clasped or closed position to secure the XR grasp controller 102 against the hand of a user.

In one example, the biometric sensor 210 may be a heart rate sensor, a galvanic skin response (GSR) sensor, an electromyography (EMG) sensor, and the like. The XR grasp controller 102 may include different sensors in different legs 204. For example, a biometric sensor 210 on leg $204_1$ may be a GSR sensor, a biometric sensor 210 on leg $204_2$ may be a heart rate sensor, a biometric sensor 210 on leg $204_3$ may be an EMG sensor, and the like. In one example, the XR grasp controller 102 may include a single biometric sensor 210 in one of the legs 204 and other biometric sensors 210 may be located in the body portion 202.

In one example, the biometric sensors 210 may measure or collect biometric data of the user. The biometric data may be transmitted to the processor 110 of FIG. 1 and analyzed by the processor 110. The processor 110 may adjust the XR application in response to biometric data. For example, if the heart rate is too high, the amount of haptic feedback may be adjusted, the volume may be lowered, the realism of the XR application may be reduced, and so forth.

In one example, one or more of the legs 204 may also include a motion detector $212_1$ to $212_m$ (hereinafter also referred to individually as a motion detector 212 or collectively as motion detectors 212). The motion detectors 212 may be coupled along a side of each one of the legs 204 to contact the fingers of the user when the legs 204 are positioned between the fingers of the user.

In one example, the motion detectors 212 may detect the motion of the fingers of the user to provide control inputs to the computing device 106 for the XR application. For example, the control inputs may be to control a virtual hand in the XR environment, to control a pointer in the XR application, to cycle through and/or make selections in menus in the XR application, and the like.

In one example, a motion detector 212 may be a capacitive sensor that can detect motion of the fingers of the user. In one example, a motion detector 212 may be an electro-mechanical sensor. For example, the motion detector 212 may be deployed as a mechanical wheel on the side of a leg 204. The wheel may contact the side of the finger of the user. As the finger moves up the wheel may rotate upward, or as the finger moves down the wheel may rotate downward. The direction of rotation and the amount of rotation may be transmitted to the processor 206 and the processor 206 may translate the movement of the wheel into a control input for the XR application.

In one example, a biometric sensor 210 may be deployed as a motion detector 212. For example, a motion detector 212 may be an EMG sensor. The EMG sensor may detect activation of certain muscles within the fingers of the user. Thus, the EMG sensor may be used to collect biometric data and provide motion detection of the fingers of the user.

In one example, a motion detector 212 may also include an accelerometer. As a result, the motion detector 212 may also detect overall movement of the hand of the user. For example, the motion detector 212 may detect the acceleration (e.g., jerking the hand suddenly) of the hand.

Figure 3:
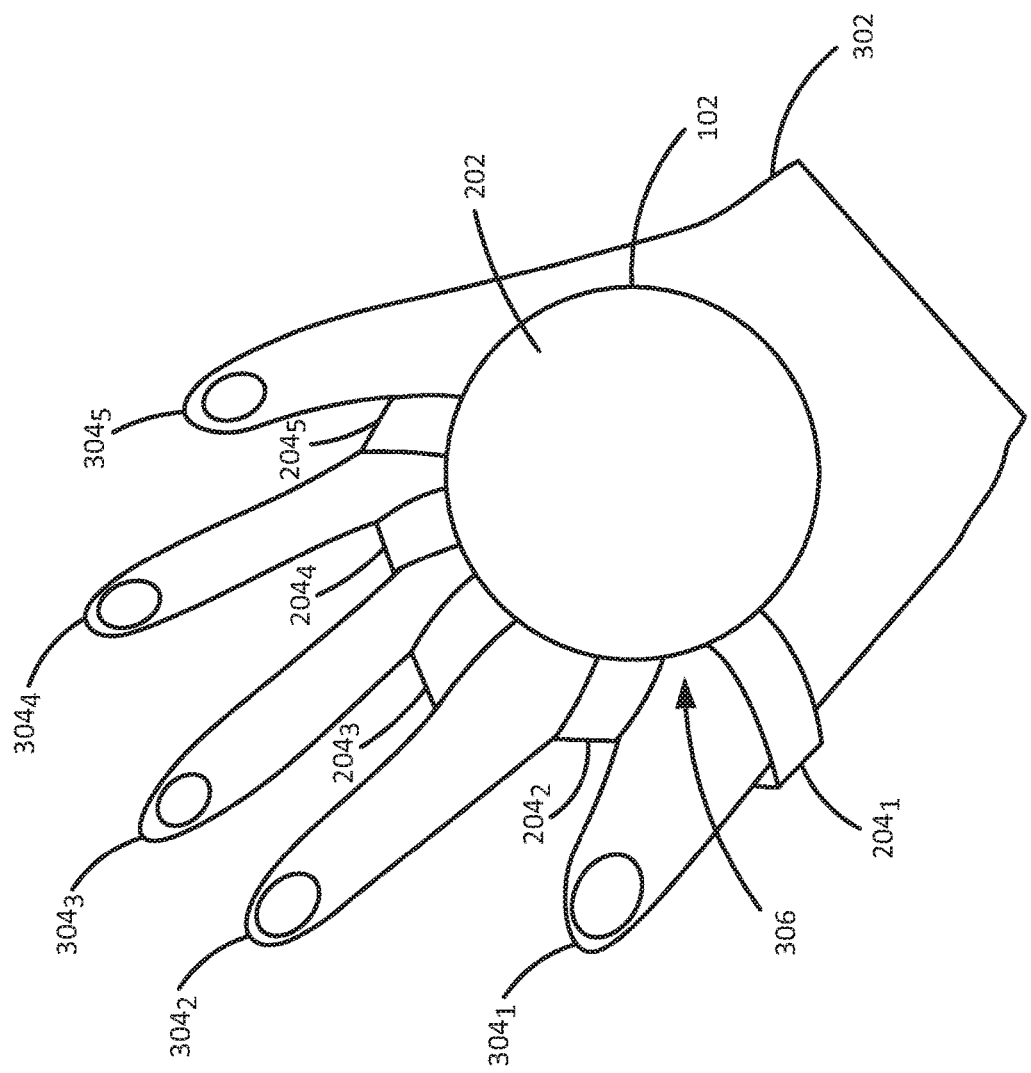
FIG. 3 is a top view of the XR grasp controller on a hand of a user of the present disclosure.

FIG. 3 illustrates a top view of the XR grasp controller 102 worn on a hand 302 of a user. The body portion 202 may rest on a backside 306 of the hand 302 of the user. As noted above, the body portion 202 may include a haptic feedback sensor that may contact the backside 306 of the hand 302 of the user.

The legs 204 may be movably coupled to the body portion 202. The legs 204 may be arranged such that the legs 204 fit between the fingers $304_1$-$304_5$ of the user. For example, the leg $204_2$ may fit between fingers $304_1$ and $304_2$. The leg $204_3$ may fit between the fingers $304_2$ and $304_3$. The leg $204_4$ may fit between the fingers $304_3$ and $304_4$. The leg $204_5$ may fit between the fingers $304_4$ and $304_5$. The leg $204_1$ may wrap around the finger $304_1$.

Figure 4:
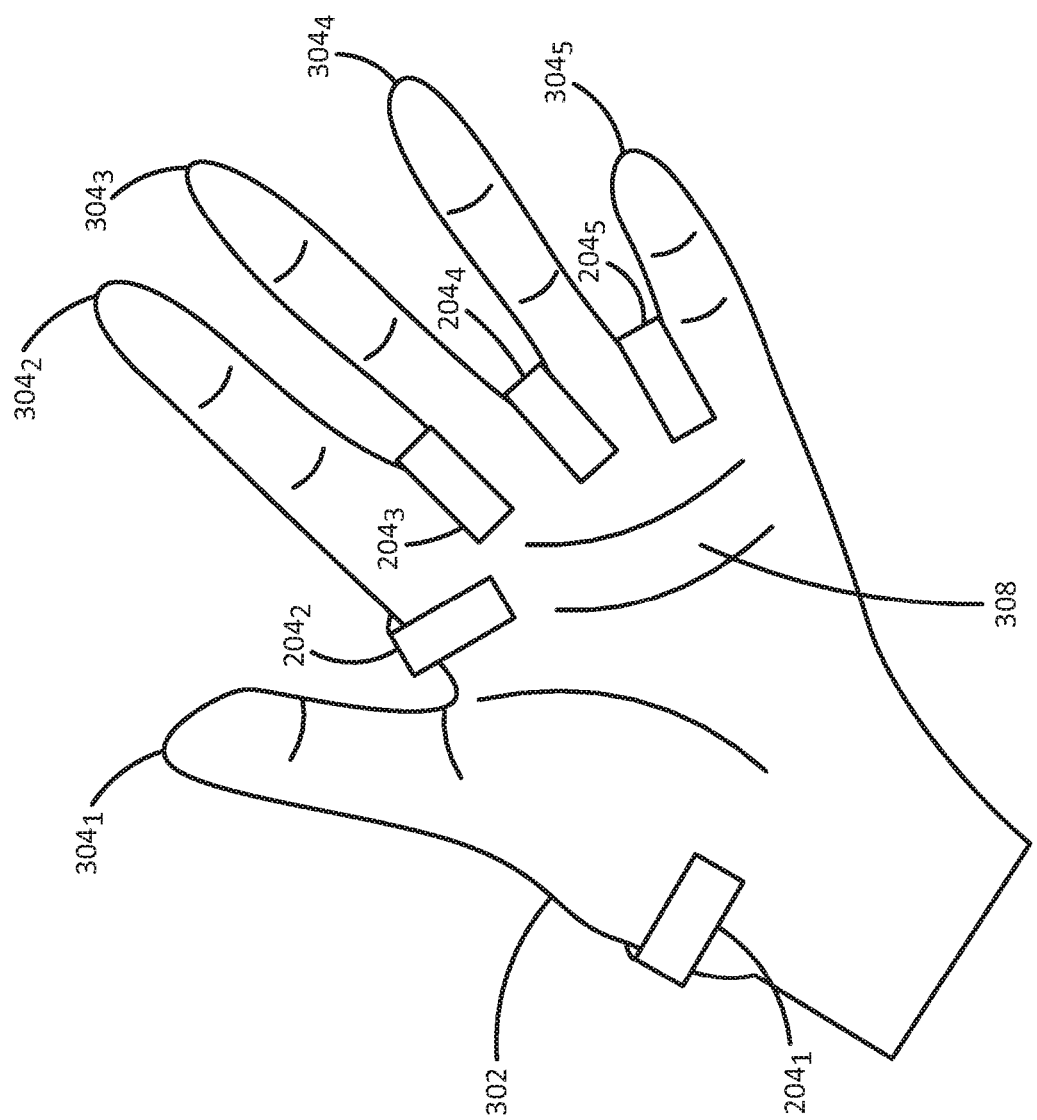
FIG. 4 illustrates a bottom view of the XR grasp controller on the hand of the user of the present disclosure.

FIG. 4 illustrates a bottom view of the XR grasp controller 102 on the hand 302 of a user. Each of the legs 204 may have a curved portion that may move between an open position and a clasped or closed position. FIG. 4 illustrates the legs 204 in the closed position and secured to the hand 302 of the user. The ends or tips of the legs 204 may be pressed against a palm 308 of the hand 302 of the user.

As discussed above, at least one of the legs 204 may include a biometric sensor 210. Some of the biometric sensors 210 may operate best when in contact with the palm 308. The design of the legs 204 allows the biometric sensors 210 to be positioned properly against the palm 308 to provide accurate measurements of some biometric data of the user.

It should be noted that the length of the legs 204 is illustrated as an example in FIG. 4. For example, the legs 204 may be longer to reach further towards a center of the palm 308, or may be shorter to be moved further away from the center of the palm 308.

In one example, the legs 204 may be opened and closed through a variety of different materials and/or mechanisms that are illustrated in FIGS. 5-7 and discussed in further details below. FIG. 5 illustrates a side view of an example of an open position 500 and a closed position 502 of legs 504. The legs 504 may be similar to the legs 204 in the number of legs that are deployed, the positioning of the legs, and the inclusion of a biometric sensor 210.

In one example, the leg 504 may have generally curved shape. The leg 504 may be cylindrical for comfort when positioned between the fingers 304 of the hand 302 of the user. However, it should be noted that the leg 504 may have any shape that may fit between the fingers 304 of the hand 302 of the user.

In one example, the leg 504 may be a single continuous piece fabricated from a shape morphing material. The shape morphing material may move when exposed to heat. For example, the shape morphing material may contract when exposed to heat emitted from the palm of a user.

For example, in the open position 500, the user may place the XR grasp controller 102 over the back of the hand 302 of the user. The ends of the legs 504 may be positioned to not contact the palm 308 of the hand 302. However, heat from other portions of the hand 302 (e.g., between the fingers 304, top portion of the palm 308, and the like) that contact the leg 504 may cause the leg 504 to contract into the closed position 502. In the closed position 502, the tips of the legs 504 may contact the palm 308 of the hand 302. For example, FIG. 5 illustrates dashed lines 506 that show how the leg 504 has moved by an amount 508 into the closed position 502.

The shape morphing material may be opened by applying enough force to overcome the contraction from the heat. Thus, the user may simply pull away the legs 504 to remove the XR grasp controller 102.

FIG. 6 illustrates a side view of an example of an open position 600 and a closed position 602 of legs 604. The legs 604 may be similar to the legs 204 in the number of legs that are deployed, the positioning of the legs, and the inclusion of a biometric sensor 210.

In one example, the legs 604 may include multiple members that are movably coupled together via joints 606. The joints 606 may be electro-mechanical. In other words, the joints 606 may include mechanically moving parts that can be controlled via an electrical signal (e.g., via the processor 206 in the body portion 202). In one example, a switch 608 may be deployed to move the legs 604 from the open position 600 to the closed position 602, and vice versa.

In one example, the switch 608 may be a physical switch. For example, the switch 608 may be a button or a slider tab that moves the legs 604 between the open position 600 and the closed position 602. In another example, the switch 608 may be a software enabled switch. For example, a selection may be toggled in a menu in a graphical user interface of the XR application when the XR grasp controller 102 is communicatively coupled to the computing device 106 or the HMD 104.

In one example, the respective tips or ends of the legs 604 may include a pressure sensor. The pressure sensor may allow the legs 604 to stop when the amount of pressure (caused by pressing against the palm 308) applied by the user is greater than a threshold. Thus, when the XR grasp controller 102 is first worn, a sizing process may be executed to determine where the legs 604 should stop in the closed position 602 for the hand 302 of a particular user. As a result, legs 604 may be designed to fit any sized hand.

In one example, the settings for the legs 604 (e.g., the position of the legs 604 when the amount of pressure is greater than a threshold) may be stored in memory. As a result, when the switch 608 is toggled to move the legs 604 in the closed position, the legs 604 may move to the correct position for the user.

FIG. 7 illustrates a side view of an example of a default position 700 and a second position 702 of legs 704. The legs 704 may be similar to the legs 204 in the number of legs that are deployed, the positioning of the legs, and the inclusion of a biometric sensor 210.

In one example, the legs 704 may include spring loaded joints 706. As shown in the default position 700, springs in the legs 704 may cause the legs 704 to contract into a closed position in the default position 700.

A force 710 may be applied against the spring loaded joints 706 to straighten out the legs 704 and allow the XR grasp controller 102 to be fitted over the hand 302 of a user.

FIG. 7 illustrates dashed lines 708 in the second position 702 of how the legs 704 are moved from the contracted position to the open position when exposed to the force 710.

When the force 710 is removed, the spring loaded joints 706 may contract back to the default position 700. The spring loaded joints 706 may pull the tips of the legs 704 up towards the body portion 202. As a result, the tips of the legs 704 may press against the palm 308 of the hand 302 and secure the XR grasp controller 102 to the hand 302 of the user.

It will be appreciated that variants of the above-disclosed and other features and functions, or alternatives thereof, may be combined into many other different systems or applications. Various presently unforeseen or unanticipated alternatives, modifications, variations, or improvements therein may be subsequently made by those skilled in the art which are also intended to be encompassed by the following claims.

The invention claimed is:

1. An apparatus, comprising:
    a body portion to rest on a backside of a hand of a user; and
    a plurality of legs movably coupled to the body portion, wherein each one of the plurality of legs comprise a curved portion to fit between fingers of a user and respective ends of the plurality of legs are to contact a palm of the user, wherein the plurality of legs comprises at least one of: a shape morphing material that contracts when in contact with heat from the palm of the user to close, electro-mechanical joints coupled to a switch to open and close the plurality of legs, or spring loaded joints.

2. The apparatus of claim 1, wherein at least one leg of the plurality of legs comprises a biometric sensor.

3. The apparatus of claim 2, wherein the at least one leg of the plurality of legs is moved to position the biometric sensor to collect biometric information of the user when the plurality of legs are in a clasped position.

4. The apparatus of claim 3, wherein the biometric sensor comprises the EMG sensor and the EMG sensor is to detect movement of the hand of the user and provide motion information for an extended reality (XR) application.

5. The apparatus of claim 2, wherein the biometric sensor comprises at least one of: a heart rate sensor, a galvanic skin response sensor, or an electromyography (EMG) sensor.

6. An apparatus, comprising:
    a body portion, the body portion, comprising:
        a haptic feedback device to provide haptic feedback, wherein the haptic feedback device is located on a bottom side of the body portion to contact a back of a hand of a user; and
        a processor in communication with the haptic feedback device, to control operation of the haptic feedback device;
    a biometric sensor in communication with the processor to collect biometric data;
    a plurality of legs movably coupled to the body portion, wherein each one of the plurality of legs comprise a curved portion to fit between fingers of a user and to contact a palm of the user; and
    a motion detector coupled to each one of the plurality of legs and in communication with the processor to detect movement of the fingers of the user.

7. The apparatus of claim 6, wherein the haptic feedback device comprises a transcutaneous electrical nerve stimulation (TENS) electrode.

8. The apparatus of claim 6, wherein the movement of the fingers is transmitted to the processor to control a virtual hand in a virtual reality environment.

9. An apparatus, comprising:
- a body portion, the body portion, comprising:
  - a haptic feedback device to provide haptic feedback, wherein the haptic feedback device is located on a bottom side of the body portion to contact a back of a hand of a user; and
  - a processor in communication with the haptic feedback device, wherein the processor is to control the haptic feedback device;
- a plurality of legs movably coupled to the body portion, wherein each one of the plurality of legs comprise a curved portion to fit between fingers of a user and contact a palm of the user;
- a motion detector coupled to each one of the plurality of legs and in communication with the processor to detect movement of the fingers of the user; and
- a biometric sensor coupled to a tip of at least one of the plurality of legs, wherein the biometric sensor contacts the palm of the user to collect biometric data.

10. The apparatus of claim 9, wherein each one of the plurality of legs comprise a pressure sensor to stop moving when an amount of pressure against the palm of the user is greater than a threshold.

11. The apparatus of claim 9, wherein the apparatus is communicatively coupled to a virtual reality system or virtual reality head mounted display.

\* \* \* \* \*